(12) United States Patent
Kim et al.

(10) Patent No.: US 10,596,799 B2
(45) Date of Patent: Mar. 24, 2020

(54) SENSING DEVICE CAPABLE OF DETECTING HARDNESS, MOBILE DEVICE HAVING THE SAME, AND THREE-DIMENSIONAL PRINTING APPARATUS USING THE SAME

(71) Applicant: SAMSUNG ELECTRONICS CO., LTD., Suwon-si, Gyeonggi-do (KR)

(72) Inventors: Dong-ki Kim, Seoul (KR); Jei-young Lee, Yongin-si (KR); Young-hwan Kim, Hwaseong-si (KR); Min-woo Seo, Seongnam-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 403 days.

(21) Appl. No.: 15/414,933

(22) Filed: Jan. 25, 2017

(65) Prior Publication Data
US 2017/0217101 A1  Aug. 3, 2017

(30) Foreign Application Priority Data

Jan. 29, 2016 (KR) ........................ 10-2016-0011452

(51) Int. Cl.
*B29C 67/00* (2017.01)
*B33Y 50/02* (2015.01)
(Continued)

(52) U.S. Cl.
CPC ............ *B33Y 10/00* (2014.12); *B29C 64/106* (2017.08); *B29C 64/321* (2017.08);
(Continued)

(58) Field of Classification Search
CPC ..... B29C 67/0088; B33Y 30/00; B33Y 50/02; G01N 29/04; G01N 3/40
See application file for complete search history.

(56) References Cited

U.S. PATENT DOCUMENTS 3,822,588 A * 7/1974 Knight ..................... G01N 3/40
73/81
2005/0061062 A1 * 3/2005 Kaneko ................ G01N 33/025
73/78
(Continued)

FOREIGN PATENT DOCUMENTS

JP    3739086    11/2005
JP    3866602    10/2006
(Continued)

OTHER PUBLICATIONS

Search Report and Written Opinion dated May 1, 2017 in counterpart International Patent Application No. PCT/KR2017/000845.

*Primary Examiner* — Nahida Sultana
(74) *Attorney, Agent, or Firm* — Nixon & Vanderhye P.C.

(57) ABSTRACT

A sensing device capable of detecting hardness includes a sensor array including a plurality of sensors, each of the plurality of sensors including a transmitter configured to emit a detection wave and a receiver configured to receive a reflected detection wave reflected by an object, the plurality of sensors arranged in a matrix form; and a controller configured to obtain image information and hardness information of each portion of the object from the reflected waves received by the plurality of sensors, and to form three-dimensional print data by mapping the image information and the hardness information.

20 Claims, 14 Drawing Sheets

(51) Int. Cl.
*G01N 29/04* (2006.01)
*G01N 29/44* (2006.01)
*B33Y 10/00* (2015.01)
*G01N 29/34* (2006.01)
*G01N 29/06* (2006.01)
*G01N 29/11* (2006.01)
*B29C 64/106* (2017.01)
*B29C 64/393* (2017.01)
*B29C 64/321* (2017.01)
*B29C 64/386* (2017.01)
*B33Y 30/00* (2015.01)
*G01N 3/40* (2006.01)
*G01N 21/3563* (2014.01)
*G01N 21/3581* (2014.01)

(52) U.S. Cl.
CPC ......... *B29C 64/386* (2017.08); *B29C 64/393* (2017.08); *B33Y 30/00* (2014.12); *B33Y 50/02* (2014.12); *G01N 3/40* (2013.01); *G01N 21/3563* (2013.01); *G01N 21/3581* (2013.01); *G01N 29/04* (2013.01); *G01N 29/0654* (2013.01); *G01N 29/11* (2013.01); *G01N 29/348* (2013.01); *G01N 29/4454* (2013.01); *G01N 2203/0055* (2013.01); *G01N 2203/0647* (2013.01); *G01N 2203/0658* (2013.01); *G01N 2291/015* (2013.01); *G01N 2291/02827* (2013.01); *G01N 2291/106* (2013.01)

(56) References Cited

U.S. PATENT DOCUMENTS

| | | |
|---|---|---|
| 2009/0169112 A1 | 7/2009 | Inoue et al. |
| 2011/0222081 A1 | 9/2011 | Yi et al. |
| 2014/0117585 A1* | 5/2014 | Douglas ............... B33Y 30/00 264/401 |
| 2014/0121813 A1 | 5/2014 | Schmehl |
| 2014/0176535 A1 | 6/2014 | Krig |
| 2014/0214205 A1 | 7/2014 | Kwon et al. |
| 2014/0272103 A1 | 9/2014 | Prince |
| 2015/0064047 A1 | 3/2015 | Hyde et al. |
| 2015/0217515 A1 | 8/2015 | Kim et al. |
| 2015/0331402 A1* | 11/2015 | Lin .................... G06F 17/5009 700/119 |
| 2017/0120527 A1* | 5/2017 | Miller .................. A43B 13/00 |
| 2017/0180652 A1* | 6/2017 | Baca .................. G06K 9/00771 |
| 2018/0214096 A1* | 8/2018 | Pascal ................. A61B 6/4233 |
| 2019/0014309 A1* | 1/2019 | Fei ......................... B33Y 10/00 |

FOREIGN PATENT DOCUMENTS

| | | |
|---|---|---|
| KR | 10-2009-0071440 | 7/2009 |
| KR | 10-2014-0096692 | 8/2014 |

* cited by examiner

SENSING DEVICE CAPABLE OF DETECTING HARDNESS, MOBILE DEVICE HAVING THE SAME, AND THREE-DIMENSIONAL PRINTING APPARATUS USING THE SAME

CROSS-REFERENCE TO RELATED APPLICATION

This application is based on and claims priority under 35 U.S.C. § 119 to Korean Patent Application No. 10-2016-0011452 filed Jan. 29, 2016 in the Korean Intellectual Property Office, the disclosure of which is incorporated by reference herein in its entirety.

BACKGROUND

1. Field

The present disclosure relates generally to a sensing device capable of obtaining three-dimensional print data and a three-dimensional printing apparatus using the same. For example, the present disclosure relates to a sensing device capable of hardness detection that can obtain three-dimensional print data including hardness information, a mobile device having the same, and a three-dimensional printing apparatus using the same.

2. Description of Related Art

According to the development of electronic technology, an imaging device or a sensing device capable of obtaining a three dimensional image of an object has been developed and widely used.

However, a conventional sensing device capable of obtaining a three-dimensional image cannot obtain information about hardness or stiffness of the object, that is, a degree of hardness or stiffness of the object.

Accordingly, when a three-dimensional image obtained by the conventional sensing device is printed using a three-dimensional printing apparatus, an output having the same shape as the object can be obtained. However, since the hardness information of the object is not included in the three-dimensional image data of the object obtained by the conventional sensing device, the output of the object is formed such that all portions of the output have the same hardness.

For example, when a three-dimensional image of an apple is obtained by the conventional sensing device and is printed by the conventional three-dimensional printing apparatus, an output having a shape similar to that of the captured apple may be obtained. The printed apple is formed of a material having a single hardness.

However, since peel, pulp, and seeds of a real apple are different in the hardness, there is a problem that an apple having similar hardness to the real apple cannot be formed by the three-dimensional image and the three-dimensional printing apparatus according to the related art.

In other words, there is a problem in that when an object is composed of parts having various hardness, the conventional sensing device capable of obtaining a three-dimensional image may not recognize hardness of various portions of the object.

SUMMARY

The present disclosure has been developed to address the above drawbacks and other problems associated with the conventional arrangement. An example aspect of the present disclosure relates a sensing device capable of detecting hardness that can obtain three-dimensional print data including hardness information, a mobile device having the same, and a three-dimensional printing apparatus using the same.

According to an example aspect of the present disclosure, a sensing device capable of detecting hardness may include a sensor array including a plurality of sensors arranged in a matrix form; and a controller configured to obtain image information and hardness information of each portion of an object from reflected waves received by the plurality of sensors, and to form three-dimensional print data by mapping the image information and the hardness information.

The plurality of sensors of the sensor array may be arranged in a plane.

The plurality of sensors of the sensor array may be arranged in a hollow cylindrical shape.

The sensor array may include a plurality of sensors provided to cover one end of the hollow cylindrical shape.

The sensing device capable of detecting hardness may include a plurality of camera modules provided in the sensor array, wherein the controller may be configured to obtain color information of each portion of the object from the plurality of camera modules.

The sensor array may include a plurality of first sensors configured to emit a first detection wave, and a plurality of second sensors configured to emit a second detection wave different from the first detection wave.

The first detection wave may include a terahertz wave, and the second detection wave may include an ultrasonic wave.

The controller may be configured to form the three-dimensional print data by mapping the image information, the hardness information, and the color information, and to store the three-dimensional print data.

Each of the plurality of sensors may be configured to emit a detection wave including one or more of a terahertz wave, a millimeter wave, and an ultrasonic wave.

According to another example aspect of the present disclosure, a mobile device may include a camera module; a sensor array disposed adjacent to the camera module and comprising a plurality of sensors arranged in a matrix form; and a controller configured to obtain image information and hardness information of each portion of an object from reflected waves received by the plurality of sensors, to obtain color information of each portion of the object from the camera module, and to form three-dimensional print data by mapping the image information, the hardness information, and the color information.

The controller may be configured to store the three-dimensional print data formed by the print data processor.

The mobile device may include a cylindrical sensor array detachably connected to the mobile device.

The cylindrical sensor array may include a plurality of camera modules. The mobile device may include an ultrasonic sensor array unit detachably connected to the mobile device.

According to another example aspect of the present disclosure, a three-dimensional printing apparatus may include a receiver including a receiving circuit configured to receive three-dimensional print data from a sensing device capable of detecting hardness; a print controller configured to analyze the three-dimensional print data received by the receiving circuit; a material mixer configured to form a material corresponding to an analysis result of the print controller; and a print head configured to form a shape corresponding to the received three-dimensional print data using the material supplied from the material mixer, wherein the sensing device capable of detecting hardness includes a sensor array including a plurality of sensors arranged in a matrix form; and a controller configured to obtain image information and hardness information of each portion of an object from reflected waves received by the plurality of sensors, and to form three-dimensional print data by mapping image information and hardness information.

The material mixer may include a material selecting portion configured to supply a material having hardness corresponding to the analysis result of the print controller; a color selecting portion configured to supply a pigment having a color corresponding to the analysis result of the print controller; and a mixing portion configured to form a material having color and hardness corresponding to the analysis result of the print controller by mixing the material supplied from the material selecting portion and the pigment supplied from the color selecting portion.

The material selecting portion may include a plurality of material cartridges accommodating materials having different hardness.

The color selecting portion may include a plurality of pigment cartridges accommodating pigments having different colors.

The receiver may be configured to receive the three-dimensional print data from a cloud or a Web hard disk.

Other objects, advantages and salient features of the present disclosure will become apparent from the following detailed description, which, taken in conjunction with the annexed drawings, discloses various example embodiments.

BRIEF DESCRIPTION OF THE DRAWINGS

These and/or other aspects, features and advantages of the present disclosure will become apparent and more readily appreciated from the following detailed description, taken in conjunction with the accompanying drawings, in which like reference numerals refer to like elements, and wherein.

Throughout the drawings, like reference numerals will be understood to refer to like parts, components and structures.

DETAILED DESCRIPTION

Hereinafter, various example embodiments of the present disclosure will be described in greater detail with reference to the accompanying drawings.

The matters disclosed herein, such as a detailed construction and elements thereof, are provided to aid in a comprehensive understanding of this description. Thus, it is apparent that example embodiments may be carried out without those defined matters. Also, well-known functions or constructions may be omitted to provide a clear and concise description of example embodiments. Further, dimensions of various elements in the accompanying drawings may be arbitrarily increased or decreased to aid in a comprehensive understanding.

The terms "first", "second", etc. may be used to describe diverse components, but the components are not limited by the terms. The terms are only used to distinguish one component from the others.

The terms used in the present description are used to describe the example embodiments, but are not intended to limit the scope of the disclosure. The singular expression also includes the plural meaning so long as it does not conflict with the context. In the present description, the terms "include" and "consist of" designate the presence of features, numbers, steps, operations, components, elements, or a combination thereof that are written in the description, but do not exclude the presence or possibility of addition of one or more other features, numbers, steps, operations, components, elements, or a combination thereof.

In the various example embodiments of the present disclosure, a "module" or a "unit" performs at least one function or operation, and may be implemented with hardware, software, or a combination of hardware and software. In addition, a plurality of "modules" or a plurality of "units" may be integrated into at least one module except for a "module" or a "unit" which has to be implemented with specific hardware, and may be implemented with various processing circuitry, such as, for example, and without limitation, at least one processor (not shown).

The terms and words used in the following description and claims are not limited to the bibliographical meanings, but, are merely used to enable a clear and consistent understanding of the present disclosure. Accordingly, it should be apparent to those skilled in the art that the following description of various example embodiments of the present disclosure is provided for illustration purpose only and not for the purpose of limiting the present disclosure as defined by the appended claims and their equivalents.

Figure 1:
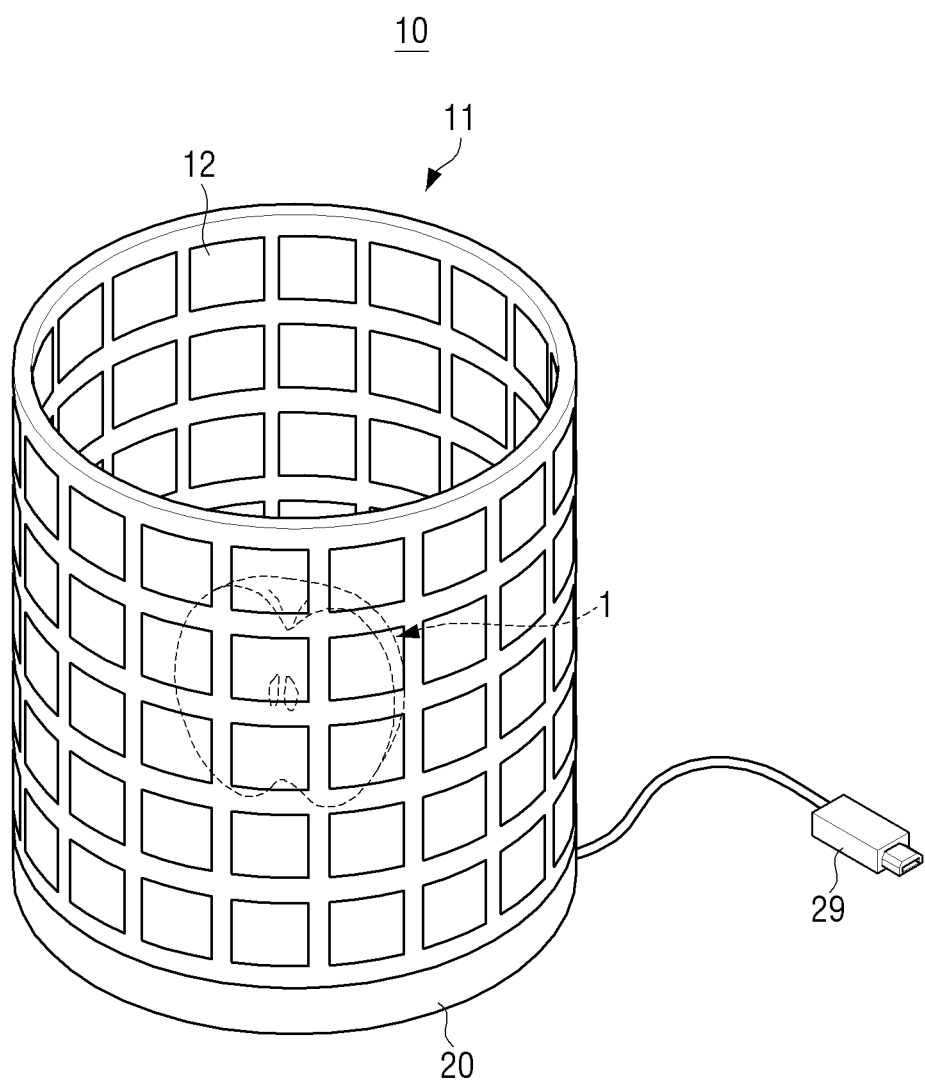
FIG. 1 is a diagram illustrating a perspective view of an example sensing device capable of detecting hardness according to an example embodiment of the present disclosure.
Figure 2:
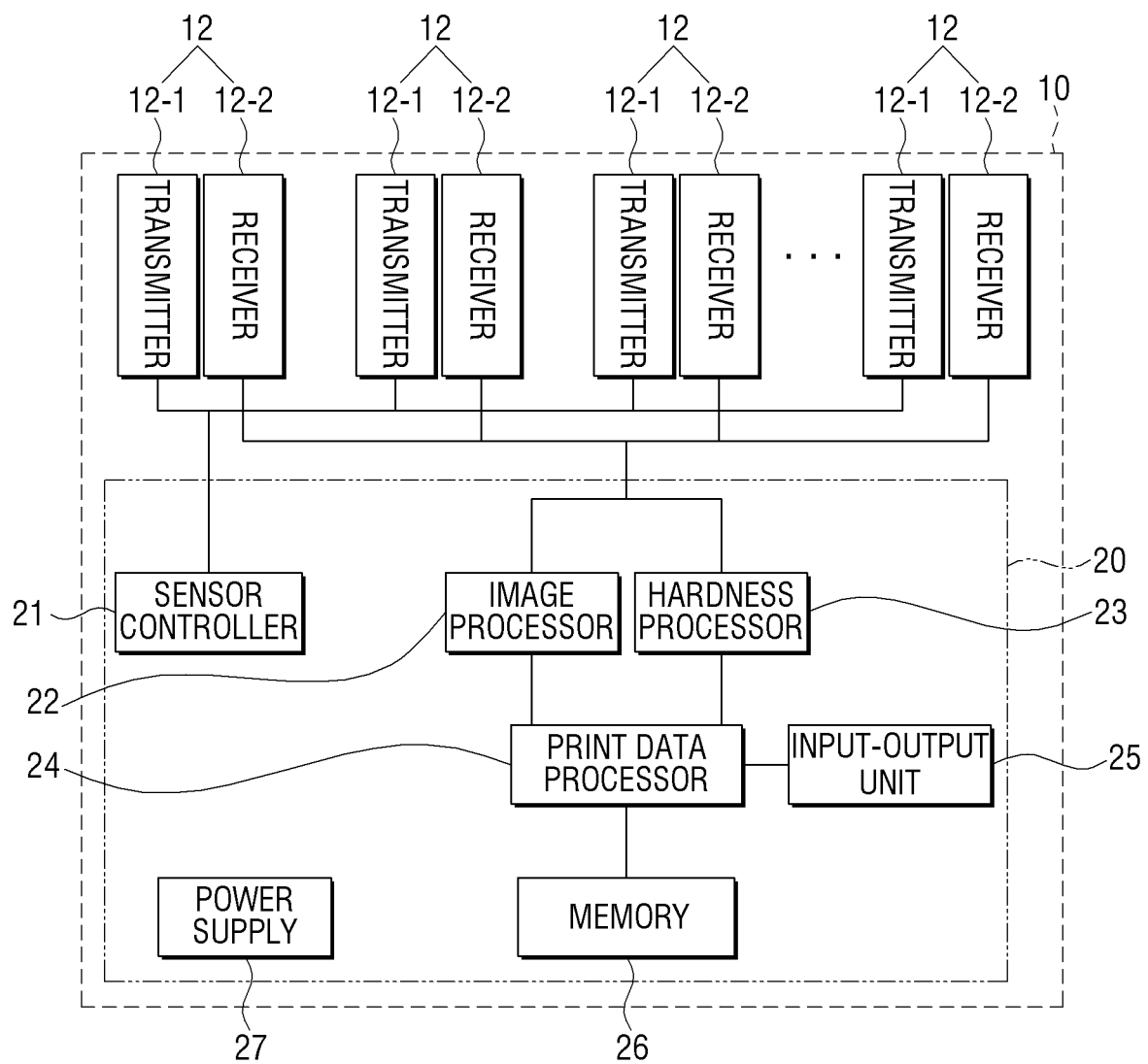
FIG. 2 is a block diagram illustrating an example sensing device capable of detecting hardness according to an example embodiment of the present disclosure.

FIG. 1 is a diagram illustrating a perspective view of an example sensing device capable of detecting hardness according to an example embodiment of the present disclosure. FIG. 2 is a block diagram illustrating an example sensing device capable of detecting hardness according to an example embodiment of the present disclosure.

Referring to FIGS. 1 and 2, a sensing device capable of detecting hardness 10 according to an example embodiment of the present disclosure may include a sensor array 11 and a controller (e.g., including processing circuitry) 20.

The sensor array 11 includes a plurality of sensors 12 capable of emitting a detection wave toward a target object 1. The plurality of sensors 12 may be arranged in a matrix form.

In an example embodiment as illustrated in FIG. 1, the plurality of sensors 12 of the sensor array 11 are arranged in a hollow cylindrical shape. Each of the plurality of sensors 12 may be provided to emit a detection wave in a horizontal direction toward the center line of the hollow cylinder. The target object 1 whose a three-dimensional image and hardness are photographed and detected by the sensing device capable of detecting hardness 10 may be positioned at the center line of the hollow cylinder. In FIG. 1, five sensors 12 are arranged in the longitudinal direction of the hollow cylinder, and eighteen sensors 12 are arranged in the circumferential direction of the hollow cylinder. However, this is only an example, and the arrangement of the plurality of sensors 12 is not limited thereto. FIG. 1 illustrates an example where the sensor array 11 photographs a half of an apple as the target object 1.

The plurality of sensors 12 may all include the same type of sensors. Each of the sensors 12 may include a transmitter 12-1 and a receiver 12-2. The transmitter 12-1 of the sensor 12 emits a detection wave under the control of a sensor controller 21, and the receiver 12-2 receives a reflected wave of the detection wave reflected from the object 1. For example, the reflected wave refers to the detection wave emitted from the transmitter 12-1 that is reflected by the object 1, and then is introduced into the receiver 12-2.

The controller 20 is configured to control the plurality of sensors 12 of the sensor array 11 to emit detection waves and to form three-dimensional print data including hardness information using the received reflected wave, and may include the sensor controller 21, an image processor 22, a hardness processor 23, a print data processor 24, an input-output unit (e.g., including input-output circuitry) 25, and a memory 26.

The controller 20 may include various electronic components such as, for example, and without limitation, processing circuitry, an ASIC, a ROM, a RAM, etc., and may be provided in a ring shape at one end of the sensor array 11.

The sensor controller 21 may include various circuitry and/or program module(s) configured to control the transmitters 12-1 of the plurality of sensors 12 based on a command input through the input-output unit 25, so that each of the plurality of sensors 12 emits the detection wave. The sensor controller 21 may be configured such that the transmitter 12-1 of the sensor 12 performs frequency sweep of the detection waves and the receiver 12-2 thereof receives the reflected waves based on the frequency sweep.

The detection wave may include a wave having a property of being reflected by an object 1 and returning toward the transmitter 12-1. For example, the detection wave may include a terahertz wave, a millimeter wave, an ultrasonic wave, a light, or the like, but is not limited thereto. Accordingly, the plurality of sensors 12 of the sensor array 11 may include a terahertz wave sensor configured to emit a terahertz wave and to receive the terahertz wave reflected by an object, a millimeter wave sensor configured to emit a millimeter wave and to receive the millimeter wave reflected by the object, an ultrasonic wave sensor configured to emit an ultrasonic wave and to receive the ultrasonic wave reflected by the object, or the like, but is not limited thereto. For example, when the frequency sweep is performed using a terahertz wave or a millimeter wave, the internal structure of the object may be recognized by analyzing the received reflected wave.

The image processor 22 may include various circuitry and/or program module(s) configured to obtain image information of each portion of the target object 1 from the reflected waves received by the receivers 12-2 of the plurality of sensors 12. The image processor 22 may form an image of the target object 1 from the image information of each portion of the target object 1 obtained by the plurality of receivers 12-2. The image processor 22 may recognize three-dimensional coordinates of image information of each portion of the target object 1. Accordingly, the image processor 22 may form, for example, a voxel-shaped image data including three dimensional coordinates of each portion of the target object 1 and the image information of the each portion. That the image processor 22 forms the image of the target object 1 using the received reflected waves will be understood by one or ordinary skill in the art; therefore, a detailed description thereof is omitted.

The hardness processor 23 may include various circuitry and/or program module(s) configured to obtain hardness information of each portion of the target object 1 from the reflected waves received by the receivers 12-2 of the plurality of sensors 12. The magnitude of the reflected wave that the detection wave is reflected on the target object 1, for example, the amplitude of the reflected wave may change based on the hardness of a portion of the target object 1 on which the detection wave is reflected. Accordingly, when the magnitude of the reflected wave is detected, the hardness of the reflected portion of the target object 1 may be detected. The relationship between the hardness of the object 1 reflecting the detection wave and the magnitude of the reflected wave is determined based on a type of the detection wave. The relationship between the hardness of objects and the magnitude of the reflected wave may be stored in advance in the hardness processor 23. Accordingly, the hardness processor 23 may determine hardness data including three dimensional coordinates of each portion of the target object 1 and hardness information of the each portion.

The print data processor 24 may include various circuitry and/or program module(s) configured to form three-dimensional print data by mapping the image data obtained from the image processor 22 and the hardness data obtained from the hardness processor 23. For example, the print data processor 24 may combine the coordinates of each portion of the three-dimensional image with hardness information corresponding to the coordinates to form three-dimensional print data including the hardness information.

As another example, when terahertz wave sensors or millimeter wave sensors are used as the plurality of sensors 12 and the frequency sweep is performed, the print data processor 24 may be configured to recognize the target object 1 by extracting the characteristic of the spectrum of the received reflected wave and comparing the characteristic of the spectrum with the database. Further, the print data processor 24 may be configured to include characteristics of the target object 1 recognized from the database, for example, texture, moisture, color, permittivity, etc. of the target object 1 in the three-dimensional print data. The database may include the characteristics of the spectrum of the received reflected wave when a frequency sweep is performed, for example, with the terahertz wave or the millimeter wave with respect to various objects. Also, the database may include texture, moisture, color, permittivity, etc. of each of the various objects.

The input-output unit 25 may include various input-output circuitry configured to output the three-dimensional print data formed by the print data processor 24 to the outside. Also, the input-output unit 25 may be configured to receive an operation command of the sensing device 10 input from the outside.

The input-output unit 25 may be connected to an external device wirelessly or by wire. For example, the input-output unit 25 may be connected to a personal computer or a mobile device by wire or wirelessly. The mobile device may include a notebook computer, a tablet computer, a smartphone, or the like, but is not limited thereto. In this case, the three-dimensional print data formed by the print data processor 24 may be stored in the external device. FIG. 1 illustrates an example in which a USB cable 29 is connected to the input-output unit 25 of the controller 20.

The input-output unit 25 may be configured to be directly connected to a cloud and a Web hard disk via the internet. In this case, the three-dimensional print data provided by the print data processor 24 may be stored in the cloud or the Web hard disk.

Figure 11:
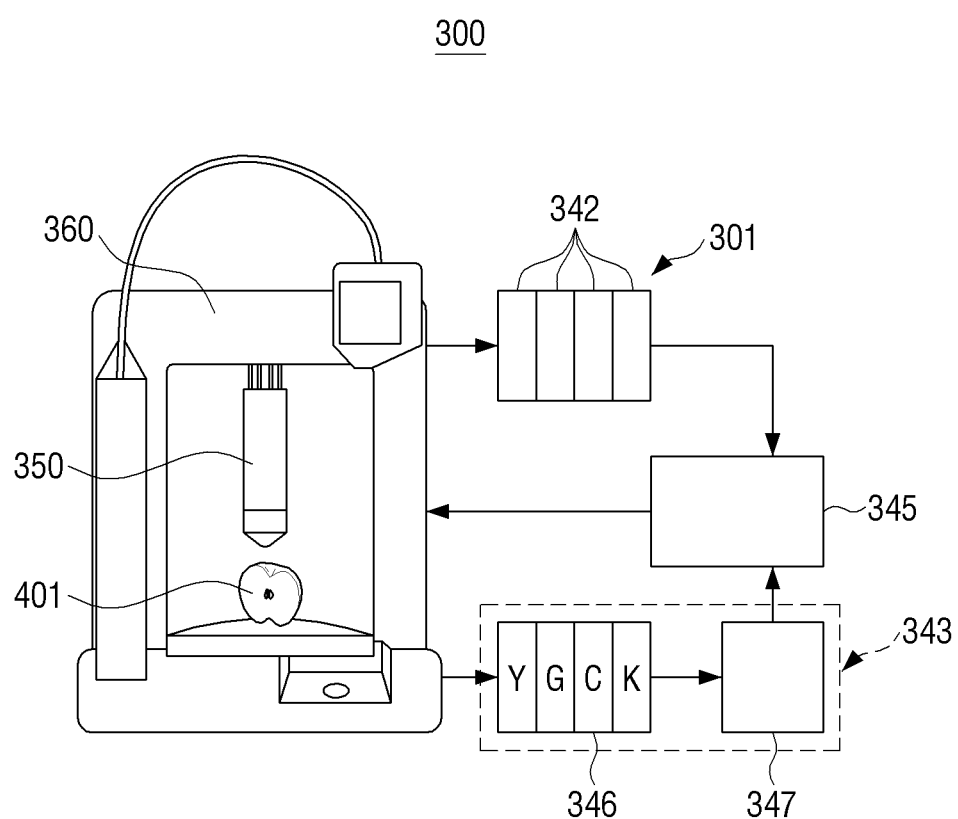
FIG. 11 is a diagram illustrating an example three-dimensional printing apparatus that can output a three-dimensional image including hardness information obtained by a sensing device capable of detecting hardness according to an example embodiment of the present disclosure.

As another example, the input-output unit 25 may be configured to be directly connected to a three-dimensional printing apparatus 300 (see FIG. 11). In this case, the three-dimensional print data provided by the print data processor 24 may be directly printed through the three-dimensional printing apparatus 300.

The memory 26 may be configured to store the three-dimensional print data provided by the print data processor 24. Accordingly, the three-dimensional print data provided by the print data processor 24 may be stored in the memory 26 without being output to the outside. Further, the three-dimensional print data stored in the memory 26 may be transmitted to the external device, the cloud, the web hard disk, and the three-dimensional printing apparatus through the input-output unit 25.

Also, the sensing device capable of detecting hardness 10 according to an example embodiment of the present disclosure may further include a power supply 27. The power supply 27 may supply power to the plurality of sensors 12 of the sensor array 11 and to the portions of the controller 20. A battery may, for example, be used as the power supply 27. As another example, it is also possible to supply power to the plurality of sensors 12 and the controller 20 through the input-output unit 25 from the outside.

In the above description, the sensor array 11 is formed, for example, as a hollow cylindrical shape. However, the sensor array 11 may be formed in a shape which one end of a hollow cylinder is covered, for example, a cylindrical container shape, as illustrated in FIG. 3.

Figure 3:
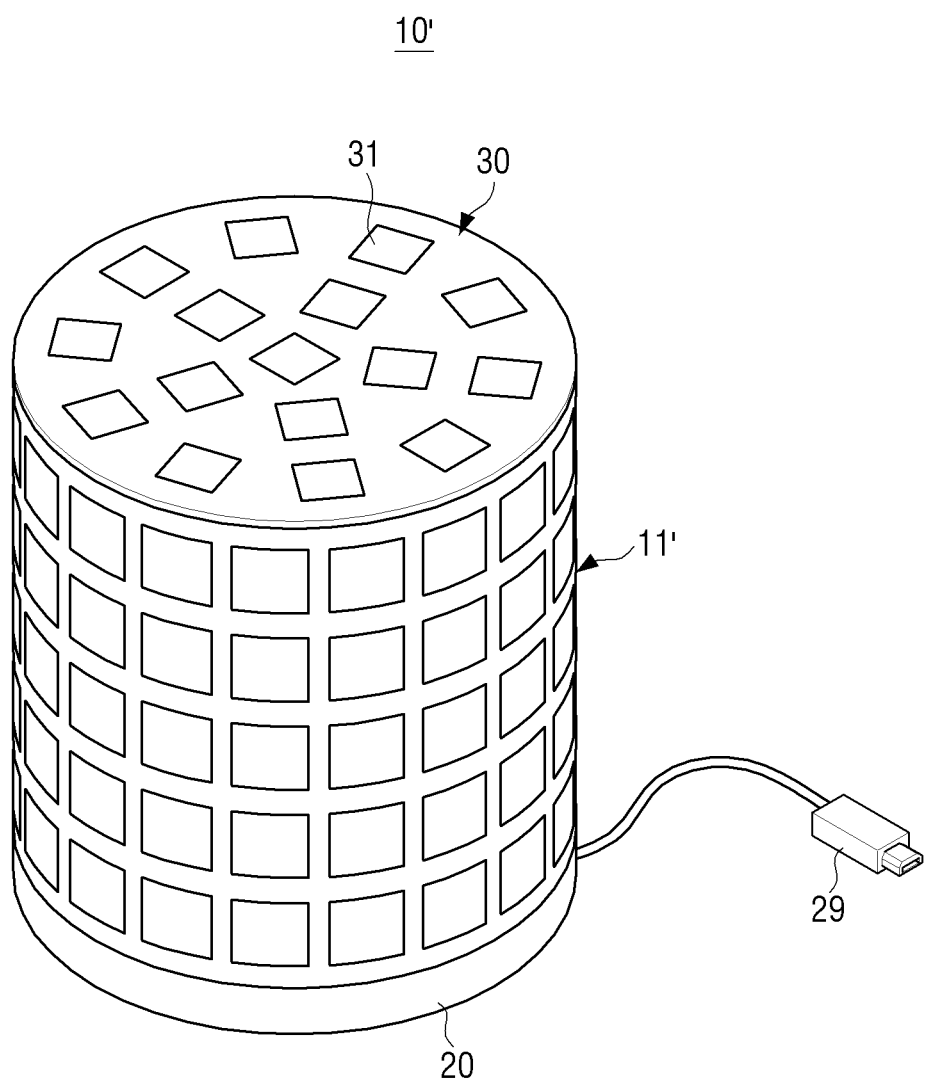
FIG. 3 is a perspective view illustrating an example sensing device capable of detecting hardness according to another example embodiment of the present disclosure.

FIG. 3 is a perspective view illustrating an example sensing device 10' capable of detecting hardness according to another example embodiment of the present disclosure, and illustrates an example in which the sensor array is formed in a cylindrical container shape.

A sensor array 11' as illustrated in FIG. 3 is the same as the sensor array 11 as illustrated in FIG. 1 except that a cover portion 30 is provided at one end of the sensor array 11 of the hollow cylindrical shape illustrated in FIG. 1.

A plurality of sensors 31 may be of the same type as the plurality of sensors 12 arranged on the side surface of the cylindrical container are disposed concentrically on the cover portion 30. Accordingly, it is possible to detect not only the periphery of a target object located at the center of the sensor array 11' as illustrated in FIG. 3, but also the upper portion of the target object.

Figure 4:
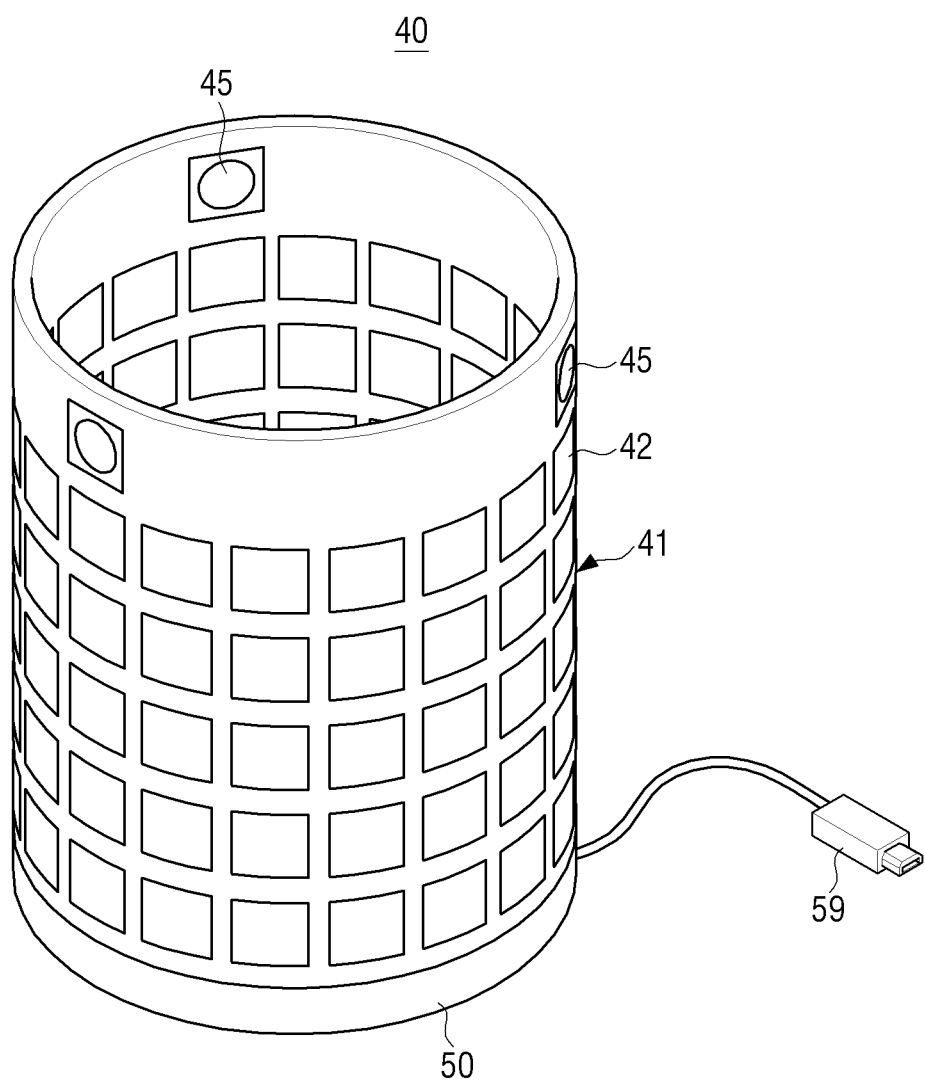
FIG. 4 is a perspective view illustrating an example sensing device capable of detecting hardness according to another example embodiment of the present disclosure.
Figure 5:
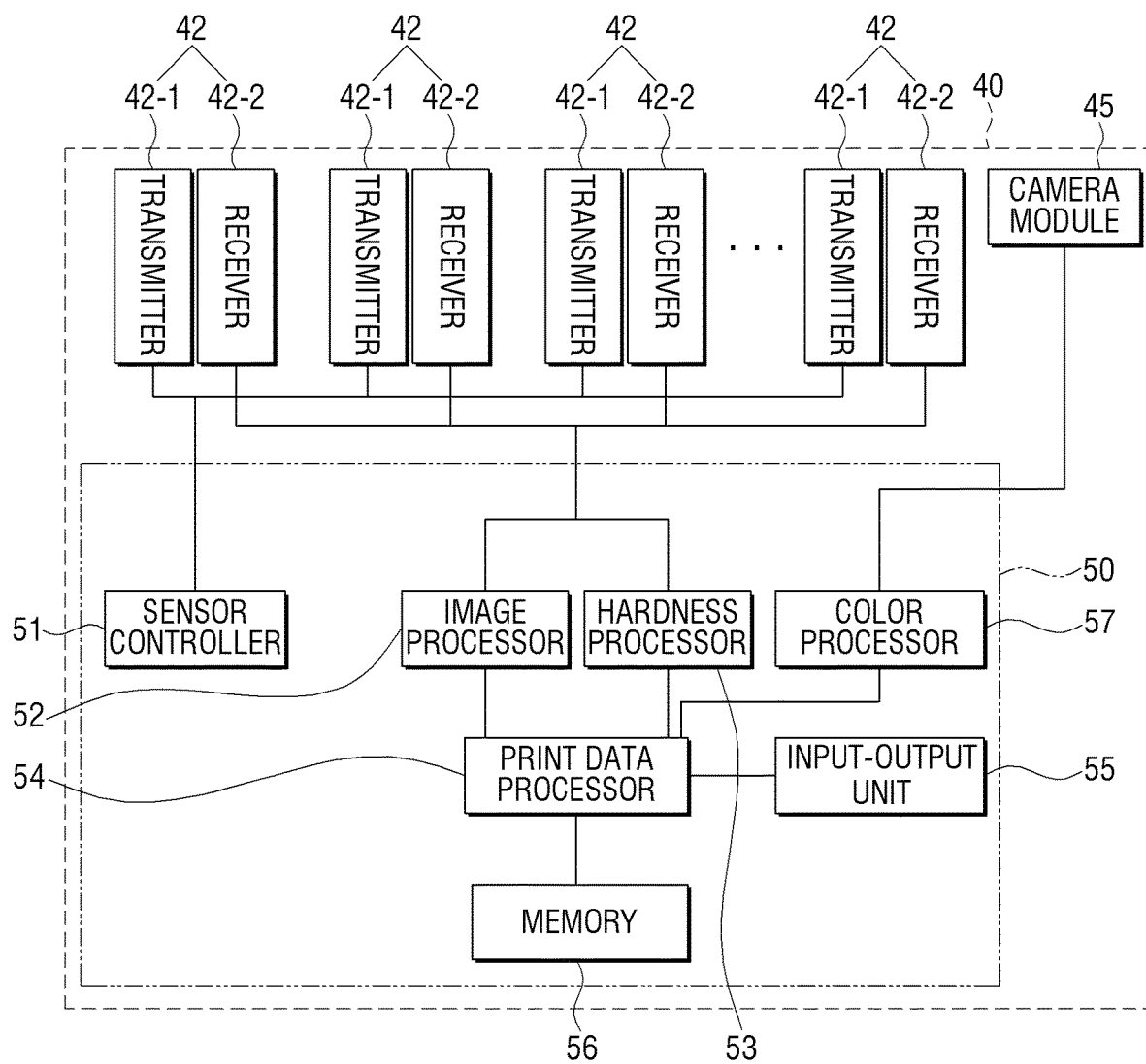
FIG. 5 is a block diagram illustrating an example sensing device capable of detecting hardness according to another example embodiment of the present disclosure.

FIG. 4 is a perspective view illustrating an example sensing device capable of detecting hardness according to another example embodiment of the present disclosure, and FIG. 5 is a block diagram illustrating an example sensing device capable of detecting hardness according to another example embodiment of the present disclosure.

Referring to FIGS. 4 and 5, a sensing device capable of detecting hardness 40 may include a sensor array 41 and a controller 50.

The sensor array 41 may include a plurality of sensors 42 capable of emitting a detection wave toward a target object and a plurality of camera modules 45. The plurality of sensors 42 may be arranged in a matrix form.

In an example embodiment as illustrated in FIG. 4, the plurality of sensors 42 of the sensor array 41 are arranged in a hollow cylindrical shape. Each of the plurality of sensors 42 may be disposed to emit a detection wave in a horizontal direction toward the center line of the hollow cylinder. In FIG. 4, five sensors 42 are arranged in the longitudinal direction of the hollow cylinder, and eighteen sensors 42 are arranged in the circumferential direction of the hollow cylinder. However, this is only an example, and the arrangement of the plurality of sensors 42 is not limited thereto.

The plurality of sensors 42 of the sensor array 11 are the same as or similar to the plurality of sensors 12 of the sensing device capable of detecting hardness 10 according to the above-described example embodiment; therefore, a detailed description thereof is omitted.

Further, the plurality of camera modules 45 may be disposed in the sensor array 41 to capture a three-dimensional image of the target object located, for example, at the center of the sensor array 41. The sensing device capable of detecting hardness 40 according to an example embodiment of the present disclosure may detect color information of the target object using the plurality of camera modules 45.

The controller 50 may include various processing circuitry and is configured to control the plurality of sensors 42 of the sensor array 41 to emit detection waves and to form three-dimensional print data including hardness information using the received reflected waves, and may include a sensor controller 51, an image processor 52, a hardness processor 53, a color processor 57, a print data processor 54, an input-output unit 55, and a memory 56.

The sensor controller 51 may include various circuitry and/or program module(s) configured to control transmitters 42-1 of the plurality of sensors 42 based on a command input through the input-output unit 55 so that each of the transmitters 42-1 of the plurality of sensors 42 of the sensor array 41 emits the detection wave, and to control receiver 42-2 of the plurality of sensors 42 to receive the reflected wave reflected from the target object. Further, the sensor controller 51 may be configured to photograph the target object by controlling the plurality of camera modules 45 provided at one end of the sensor array 41 based on a command input through the input-output unit 55. As another example embodiment, the sensor controller 51 may be configured such that the transmitters 42-1 of the plurality of sensors 42 perform frequency sweep of the detection waves and the receivers 42-2 thereof receive the reflected waves according to the frequency sweep.

The color processor 57 may include various circuitry and/or program module(s) configured to extract color information of the target object from the image captured by the plurality of camera modules 45. For example, the color processor 57 may be configured to extract three-dimensional coordinates (x, y, z) of all the portions of the target object 11 and color information corresponding to each three-dimensional coordinates from the captured image.

The image processor 52 and the hardness processor 53 may include various circuitry and/or program module(s) configured to obtain image information and hardness information of the target object using the reflected waves received by the receivers 42-2 of the plurality of sensors 42. The configurations of the image processor 52 and the hardness processor 53 to obtain the image information and the hardness information of the target object using the reflected waves received by the receivers 42-2 of the plurality of sensors 42 are similar to the image processor 22 and the hardness processor 23 of the sensing device capable of detecting hardness 10 as described above; therefore, detailed descriptions thereof will be omitted.

The print data processor 54 may include various circuitry and/or program module(s) configured to provide three-dimensional print data of the target object including image information, hardness information, and color information of the target object by mapping the three-dimensional image information, the hardness information, and the color information obtained from the image processor 52, the hardness processor 53, and the color processor 57.

The input-output unit 55 and the memory 56 are the same as or similar to the input-output unit 25 and the memory 26 of the sensing device capable of detecting hardness 10 according to the above-described example embodiment. Therefore, detailed descriptions thereof are omitted. FIG. 4 illustrates an example in which a USB cable 59 is connected to the input-output unit 55 of the controller 50.

Figure 6:
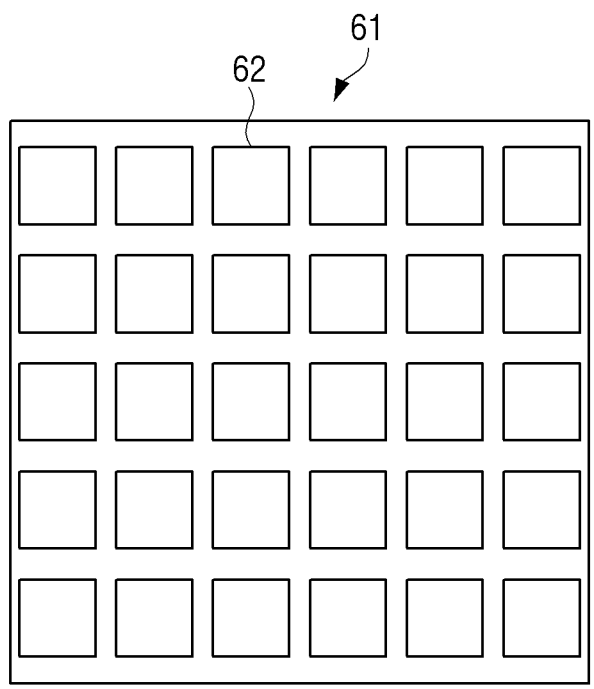
FIG. 6 is a diagram illustrating an example sensing device capable of detecting hardness according to another example embodiment of the present disclosure.

FIG. 6 is a diagram illustrating an example sensing device capable of detecting hardness according to another example embodiment of the present disclosure.

A sensing device capable of detecting hardness 60 as illustrated in FIG. 6 may be configured so that a sensor array 61 is formed in a flat plate shape. For example, a plurality of sensors 62 of the sensor array 61 are arranged substantially in a plane. The sensor array 61 as illustrated in FIG. 6 is formed substantially into a square flat plate shape. In this case, a controller (not illustrated) may be disposed behind the sensor array 61.

The configurations of the plurality of sensors 62 of the sensor array 61 and the controller of the sensing device capable of detecting hardness 60 as illustrated in FIG. 6 are the same as or similar to the plurality of sensors 12 and the controller 20 of the sensing device capable of detecting hardness 10 according to the above-described example embodiment; therefore, detailed descriptions thereof are omitted.

In the above description, the plurality of sensors 12, 42, and 62 of the various example sensor arrays 11, 41, and 61 use sensors of the same type. However, as another example embodiment, the plurality of sensors 12, 42, and 62 may include two types of sensors.

Figure 7:
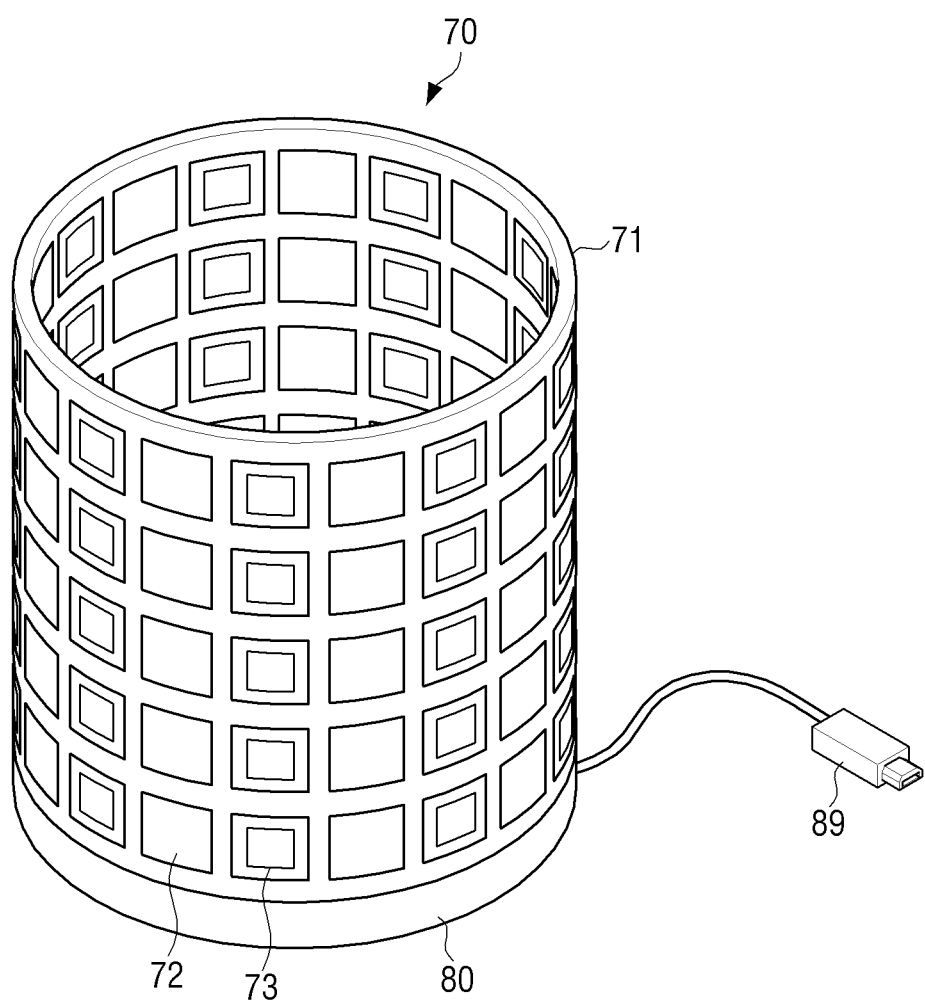
FIG. 7 is a perspective view illustrating an example sensing device capable of detecting hardness according to another example embodiment of the present disclosure.

FIG. 7 is a perspective view illustrating an example sensing device capable of detecting hardness according to another example embodiment of the present disclosure including two types of sensors.

Referring to FIG. 7, a sensing device capable of detecting hardness 70 according to an example embodiment of the present disclosure may include a sensor array 71 and a controller 80.

The sensor array 71 includes a plurality of sensors 72 and 73 arranged in a hollow cylindrical shape. The plurality of sensors 72 and 73 may include two types of sensors. For example, the sensor array 71 may be configured to include a plurality of first sensors 72 to emit a first detection wave and a plurality of second sensors 73 configured to emit a second detection wave of a different kind from the first detection wave. For example, the first sensors 72 may use a terahertz wave sensor to emit terahertz waves as the first detection wave, and the second sensors 73 may use an ultrasonic sensor to emit ultrasonic waves as the second detection wave. It will be understood that this is merely an example, and that the disclosure is not limited to these two example types of sensors.

Further, the plurality of first sensors 72 and the plurality of second sensors 73 may be alternately arranged in the circumferential direction of the sensor array 71 as illustrated in FIG. 7. In other words, five first sensors 72 may be provided in one row in the longitudinal direction of the sensor array 71, and five second sensors 73 may be provided in the next row. Five first sensors 72 may be placed again in the next row. The arrangement of the plurality of first sensors 72 and the plurality of second sensors 73 as illustrated in FIG. 7 is only one example. Therefore, the plurality of first sensors 72 and the plurality of second sensors 73 may be arranged in a variety of ways as required.

The controller 80 may include various circuitry and/or program module(s), such as, for example, and without limitation, a sensor controller, an image processor, a hardness processor, a print data processor, an input-output unit, and a memory. The sensor controller, the image processor, the hardness processor, and the print data processor are similar to the sensor controller 21, the image processor 22, the hardness processor 23, and the print data processor 24 of the sensing device capable of detecting hardness 10 according to the above-described example embodiment except that they are configured to process two types of reflected waves received by the receivers of the two types of sensors 72 and 73. Therefore, detailed descriptions thereof are omitted. Also, the input-output unit and the memory of the controller 80 may be configured in the same manner as the input-output unit 25 and the memory 26 of the sensing device capable of detecting hardness 10 according to the above-described example embodiment; therefore, the detailed description thereof is omitted. FIG. 7 illustrates an example in which a USB cable 89 is connected to the input-output unit of the controller.

In the above description, the sensing device capable of detecting hardness 10, 40, 60, and 70 is configured as a separate device. However, the sensing device capable of detecting hardness according to an example embodiment of the present disclosure may be formed integrally with a mobile device.

Hereinafter, a mobile device with a sensing device capable of detecting hardness according to an example embodiment of the present disclosure will be described in greater detail with reference to the accompanying drawings.

Figure 8:
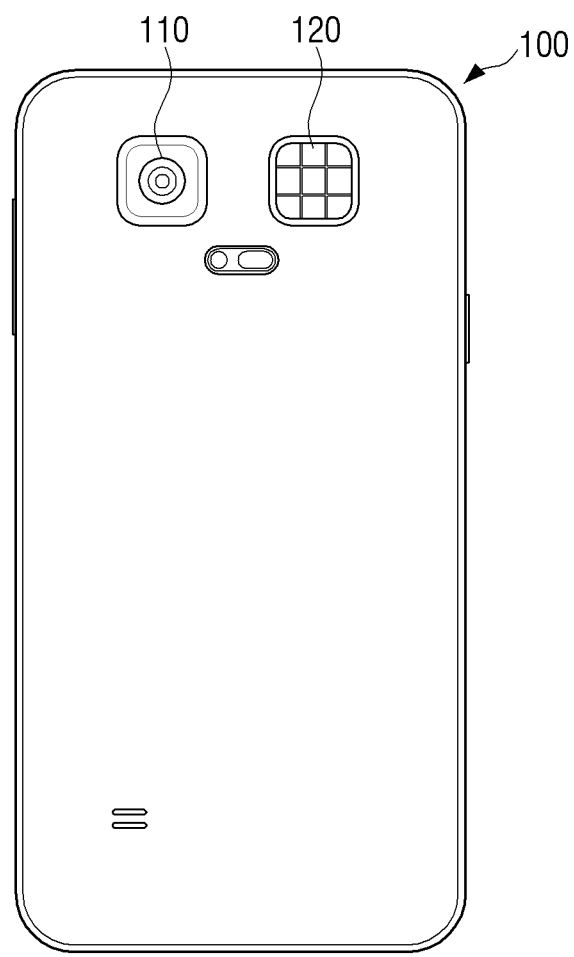
FIG. 8 is a diagram illustrating an example mobile device including a sensing device capable of detecting hardness according to an example embodiment of the present disclosure.
Figure 9:
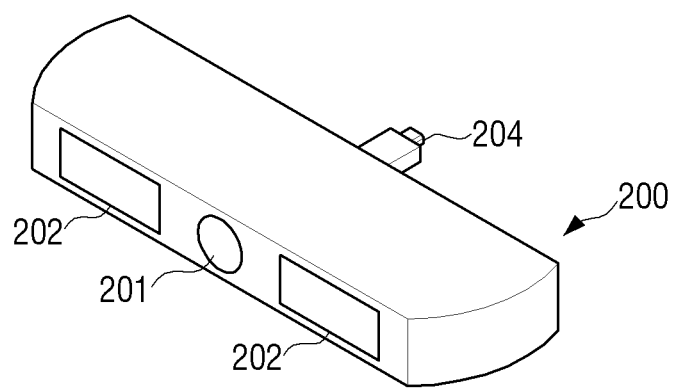
FIG. 9 is a perspective view illustrating an example ultrasonic sensor array that can be used in the mobile device of FIG. 8.

FIG. 8 is a diagram illustrating an example mobile device having a sensing device capable of detecting hardness according to an example embodiment of the present disclosure. FIG. 9 is a perspective view illustrating an example ultrasonic sensor array that can be used in the mobile device of FIG. 8.

Referring to FIG. 8, a mobile device 100 according to an example embodiment of the present disclosure may include a camera module 110 and a sensor array 120 capable of detecting hardness. FIG. 8 illustrates an example in which a smartphone is used as the mobile device 100. However, the mobile device 100 is not limited to a smartphone, but may include various types of devices that user can carry. For example, the mobile device 100 may include a notebook computer, a tablet computer, a smartphone, or the like.

The camera module 110 may include various camera circuitry and be configured to obtain color information of a target object by photographing an image of the target object. The camera module 110 is the same as or similar to a camera module that would be understood by one of ordinary skill in the art; therefore, a detailed description thereof is omitted.

The sensor array 120 may be provided adjacent to the camera module 110. In the example embodiment as illustrated in FIG. 8, the camera module 110 and the sensor array 120 are provided side by side on the rear surface of the mobile device 100.

The sensor array 120 is configured so that a plurality of sensors 121 are arranged in a matrix form in a flat plate shape. Each of the plurality of sensors 121 includes a transmitter for emitting a detection wave and a receiver for receiving a reflected wave that the emitted detection wave is reflected by an object. The plurality of sensors 121 of the sensor array 120 are the same as or similar to the plurality of sensors 12 of the sensing device capable of detecting hardness 10 according to the above-described example embodiment; therefore, a detailed description thereof is omitted.

Further, the main body of the mobile device 100 is provided with an image processor, a hardness processor, a color processor, and a print data processor for controlling the camera module 110 and the sensor array 120 and obtaining necessary information from the received reflected wave. The electronic components, such as various processing circuitry, ASICs, etc., of the image processor, the hardness processor, the color processor, and the print data processor may be disposed on a printed circuit board that is provided inside the mobile device 100.

Figure 10:
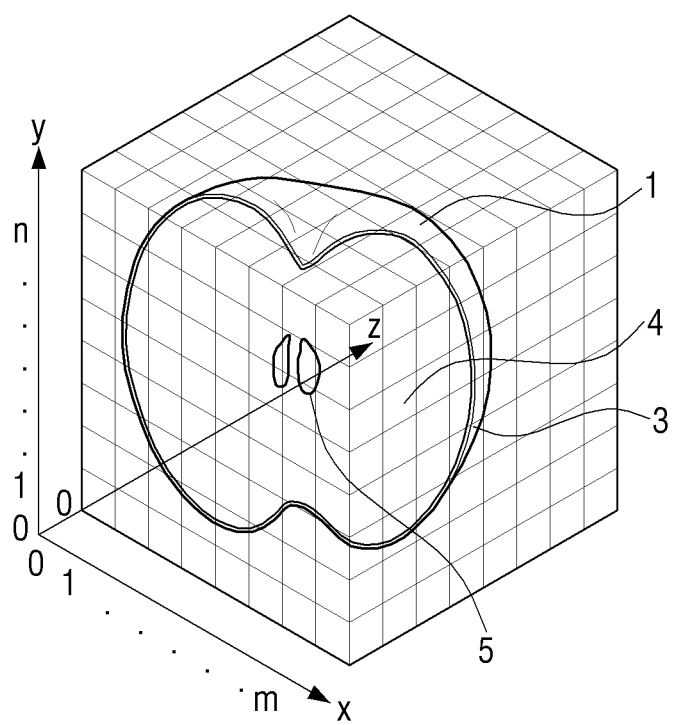
FIG. 10 is a diagram illustrating example coordinates of a three-dimensional image obtained by a sensing device capable of detecting hardness according to an example embodiment of the present disclosure.

The image processor may be configured to acquire image information of each portion of the target object from the reflected waves, that the detection wave emitted from the transmitter of each of the plurality of sensors 121 of the sensor array 120 is reflected by the target object, which is received by the receiver of each of the plurality of sensors 121, thereby obtaining three-dimensional image data of the target object. For example, each portion of the target object may refer, for example, to each divided portion when the target object 1 is placed in a coordinate space composed of X-axis, Y-axis, and Z-axis and is divided at a certain resolution as illustrated, for example in FIG. 10. All the divided portions of the target object 1 may be represented in three-dimensional coordinates (x, y, z). Accordingly, the image data obtained by the image processor may be expressed in, for example, a voxel form.

The hardness processor may be configured to obtain hardness information of each portion of the target object 1 from the above-described reflected wave received by the receivers of the plurality of sensors 121. For example, the hardness processor may be configured to acquire hardness information corresponding to the coordinates of each portion of the target object 1 acquired by the image processor from the reflected waves.

The color processor may be formed to acquire color information of each portion of the target object 1 from the image photographed by the camera module 110. For example, the color processor may be configured to obtain color information corresponding to the coordinates of each portion of the target object 1 acquired by the image processor from the image photographed by the camera module 110.

The print data processor may be configured to form three-dimensional print data by mapping the image data acquired from the image processor, the hardness information acquired from the hardness processor, and the color information acquired from the color processor.

For example, the print data processor forms image data including the hardness information by mapping the image data that are represented in the voxel form and acquired from the image processor and the hardness information acquired from the hardness processor. The image data including the hardness information may be represented by (x, y, z, A). Here, x, y, and z are coordinate values of a specific portion of the target object 1, and A represents hardness information as a magnitude of the reflected wave of the specific portion of the target object 1.

Further, the print data processor may be configured form three-dimensional print data including hardness information and color information by mapping the color information of the target object 1 acquired from the image photographed by the camera module 110 to the image data including the hardness information. The three-dimensional print data including the hardness information and the color information may be represented by (x, y, z, A, C). Here, x, y, and z are coordinate values in a voxel form of a specific portion of the target object 1, A is hardness information as a magnitude of the reflected wave of the specific portion of the target object 1, and C represents color information of the specific portion of the target object 1.

The three-dimensional print data formed by the print data processor may be stored in a storage portion of the mobile device 100, for example, a memory, a flash memory, and the like. At this time, the three-dimensional print data may be stored in the memory in a format of (address, A, C). For example, address represents a storage address of the memory in which image data of the voxel form is stored, A represents the hardness information as the magnitude of the reflected wave, and C represents the color information.

The three-dimensional print data stored in the memory of the mobile device 100 may be directly transmitted to a three-dimensional printing apparatus 300 (see FIG. 11). The mobile device 100 may be provided with a mobile print application capable of transmitting the three-dimensional print data stored in the memory to the three-dimensional printing apparatus 300 and controlling the three-dimensional printing apparatus 300 to perform printing. A user can control the three-dimensional printing apparatus 300 using the mobile print application provided in the mobile device 100, thereby printing the target object 1 corresponding to the three-dimensional print data of the target object 1 formed using the sensing device capable of detecting hardness 120 according to an example embodiment of the present disclosure and the camera module 110 in three-dimensional form.

Also, the three-dimensional print data stored in the memory of the mobile device 100 may be stored in a cloud or a Web-hard disk. If a tag is attached to an image of the three-dimensional print data stored in a cloud or a Web-hard disk, the user can easily find and print desired three-dimensional print data.

In the above description, the three-dimensional print data of the target object are formed using the sensing device capable of detecting hardness 120 built in the mobile device 100. However, using the sensing device capable of detecting hardness 120 embedded in the mobile device 100 makes it difficult to print the target object in a completely three-dimensional form. When the target object is desired to be printed in a complete three-dimensional form, a separate sensing device capable of detecting hardness that can be detachably connected to or attached to the mobile device 100 may be used.

The sensing device capable of detecting hardness that can be used by being connected to or attached to the mobile device 100 may be configured similar to the sensing device capable of detecting hardness 10 and 40 as illustrated in FIGS. 1 to 5 as described above. However, a controller of the sensing device capable of detecting hardness that may be connected to or attached to the mobile device 100 may be configured differently from the controller 20 and 50 of the sensing device capable of detecting hardness 10 and 40 as illustrated in FIGS. 1 to 5. For example, since the mobile device 100 is provided with the image processor, the hardness processor, the color processor, and the print data processor, the controller of the sensing device capable of detecting hardness, which may be connected to or attached to the mobile device 100, may be configured not to separately include these components and to use the image processor, the hardness processor, the color processor, and the print data processor provided in the mobile device 100 to form the three-dimensional print data.

A sensing device capable of detecting hardness separate from the mobile device 100, for example, an external sensing device capable of detecting hardness, may be connected to the mobile device 100 wirelessly or by wire. For example, for wireless connections, Bluetooth, WiFi, zigbee, etc. may be used.

FIG. 9 illustrates a detachable ultrasonic sensor unit 200 that can be detachably attached to the mobile device 100. A plurality of ultrasonic sensors 202 and a camera module 201 may be provided on the bottom surface of the detachable ultrasonic sensor unit 200 of FIG. 9. Also, a connecting portion (e.g., a connector) 204 that can be connected to the mobile device 100 is provided on the top surface of the detachable ultrasonic sensor unit 200, for example, the surface opposite to the surface on which the plurality of ultrasonic sensors 202 are provided. The connecting portion 204 is formed to be connectable to the connecting terminal of the mobile device 100. For example, when the mobile device 100 is provided with a USB female connector, the connecting portion 204 of the detachable ultrasonic sensor unit 200 may be provided, for example, with a USB male connector.

Accordingly, when the detachable ultrasonic sensor unit 200 as illustrated in FIG. 9 is brought into contact with the surface of the target object and then a detection wave is emitted to the target object, a three-dimensional image showing the internal structure of the target object may be obtained. The three-dimensional image obtained by the detachable ultrasonic sensor unit 200 may include hardness information of the internal structure of the target object.

A three-dimensional printing apparatus that can print a three-dimensional shape using the three-dimensional print data formed by a sensing device capable of detecting hardness according to an example embodiment of the present disclosure or a mobile device having the same will be described in greater detail with reference to FIGS. 11 and 12.

Figure 12:
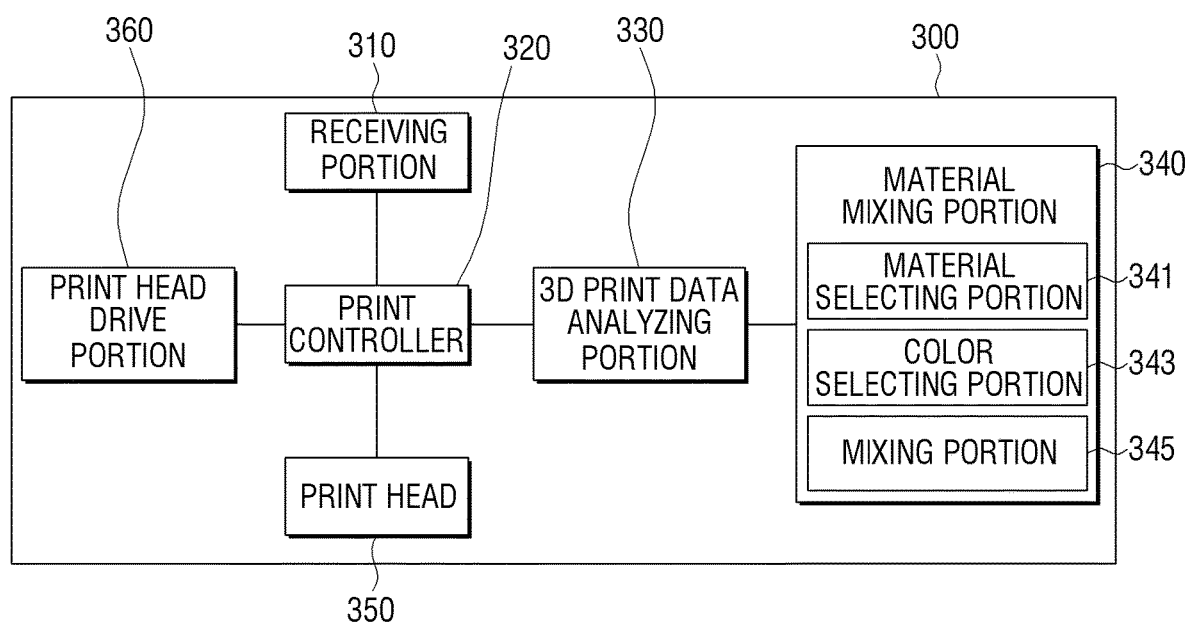
FIG. 12 is a block diagram illustrating the example three-dimensional printing apparatus of FIG. 11.

FIG. 11 is a diagram illustrating an example three-dimensional printing apparatus that can output a three-dimensional image including hardness information obtained by a sensing device capable of detecting hardness according to an example embodiment of the present disclosure, and FIG. 12 is a block diagram illustrating example the three-dimensional printing apparatus of FIG. 11.

Referring to FIGS. 11 and 12, a three-dimensional printing apparatus 300 according to an example embodiment of the present disclosure may include a receiving portion 310, a print controller 320, a three-dimensional (3D) print data analyzing portion 330, a material mixing portion 340, a print head 350, and a print head drive portion 360.

The receiving portion (or receiver) 310 may include various receiving circuitry configured to receive the three-dimensional print data including hardness information and color information from the sensing device capable of detecting hardness 10 and 40 or the mobile device 100 as described above. Also, the receiving portion 310 may be configured to receive the three-dimensional print data including the hardness information and color information from a cloud or a Web hard disk.

The print controller 320 may include various processing circuitry configured to control the receiving portion 310 to receive the three-dimensional print data from an external device such as the sensing device capable of detecting hardness 10 or the mobile device 100. Further, the print controller 320 may control the three-dimensional print data analyzing portion 330, the print head 350, and the print head drive portion 360 to print an object corresponding to the received three-dimensional print data in a three-dimensional shape.

The three-dimensional print data analyzing portion 330 may include various circuitry and/or program module(s) that analyzes the three-dimensional print data received from the receiving portion 310, determines the hardness and color of the object to be printed, and sends the hardness and color information to the material mixing portion 340. Further, the three-dimensional print data analyzing portion 330 analyzes the three-dimensional print data to be printed to determine a movement path of the print head 350, and sends the determined path to the print head drive portion 360 through the print controller 320.

The material mixing portion 340 may include a mixer configured to form a material to be used for printing in accordance with the hardness and color information of the target object sent from the three-dimensional print data analyzing portion 330. For example, the material mixing portion 340 may include a material selecting portion 341, a color selecting portion 343, and a mixing portion 345.

The material selecting portion 341 may include various elements, such as, for example, a plurality of material cartridges 342 accommodating materials having different hardness, select a material cartridge 342 filled with a material having a hardness corresponding to the analysis result of the three-dimensional print data analyzing portion 330 among the plurality of material cartridges 342, and supply the material of the material cartridge 342 to the mixing portion 345. If there is no material cartridge 342 in which a material corresponding to the hardness of the object to be printed is stored in the plurality of material cartridges 342, at least one of the plurality of material cartridges 342 may be replaced with a material cartridge 342 filled with a material having a required hardness. As the material, FDM thermoplastic resin such as ABS plus, ABSi, ABS-M30, ABS-M30i, ABS-ESDI, FDM Nylon 12, PC-ABS, PC-ISO, PPSF/PPSU, ULTEM9085, etc., or PolyJet photo-curable resin such as digital material, digital ABS, high temperature resistant resin, transparent resin, hard opaque resin, polypropylene-like resin, rubber-like resin, etc. may be used.

The color selecting portion 343 may include various elements formed to supply a pigment having a color corresponding to the analysis result of the three-dimensional print data analyzing portion 330. The color selecting portion 343 may include a plurality of pigment cartridges for receiving pigments of different colors. The color selecting portion 343 selects a pigment cartridge filled with a pigment having a color corresponding to the analysis result of the three-dimensional print data analyzing portion 330 in the plurality of pigment cartridges, and supplies the pigment of the pigment cartridge to the mixing portion 345. If there is no pigment cartridge in which a pigment corresponding to the color of the object to be printed is stored in the plurality of pigment cartridges, at least one of the plurality of pigment cartridges may be replaced with a pigment cartridge filled with a pigment having a required color.

As another example, as illustrated in FIG. 11, the color selecting portion 343 may be formed to include four color cartridges including yellow, green, cyan, and black pigments and a color mixing portion 347 that mixes pigments supplied from the yellow, green, cyan, and black color cartridges to form a pigment of required color. The color mixing portion 347 supplies a pigment having a color corresponding to the three-dimensional print data to the mixing portion 345.

The mixing portion 345 may be configured to mix the material supplied from the material selecting portion 341 and the pigment supplied from the color selecting portion 343 to form a material having color and hardness corresponding to the analysis result of the three-dimensional print data analyzing portion 330.

The material mixing portion 340 supplies the material having color and hardness corresponding to the three-dimensional print data formed in the mixing portion 345 to the print head 350.

The print head drive portion 360 may include various circuitry and/or program module(s), such as, for example, a print head driver that moves the print head 350 in accordance with the movement path of the print head 350 sent from the three-dimensional print data analyzing portion 330. For example, the print head drive portion 360 may be configured to linearly move the print head 350 in the X, Y, and Z axis directions. Also, the print head drive portion 360 may be configured to rotate the print head 350 in at least one direction. The print head 350 may be configured to rotate around three axes. The print head drive portion 360 may be configured as a rectangular coordinate robot that is formed to be linearly movable in X-axis, Y-axis, and Z-axis directions. The print head drive portion 360 may use a print head drive portion used in a conventional three-dimensional printing apparatus; therefore, a detailed description thereof is omitted.

The print head 350 may be configured to form a shape corresponding to the received three-dimensional print data using the material supplied from the material mixing portion 340. For example, the print head 350 may be formed to be connected the above-described material mixing portion 340 and to discharge the material supplied from the material mixing portion 340. Accordingly, when the print head 350 discharges the material supplied from the material mixing portion 340 while being moved by the print head drive portion 360 in a predetermined path, a shape corresponding to the three-dimensional print data is formed. The print head 350 may be controlled to be turned on or off by the print controller 320. When the print controller 320 turns on the print head 350, the material supplied from the material mixing portion 340 is discharged, and when the print head 350 is turned off, the discharging of the material is cut off.

Figure 13:
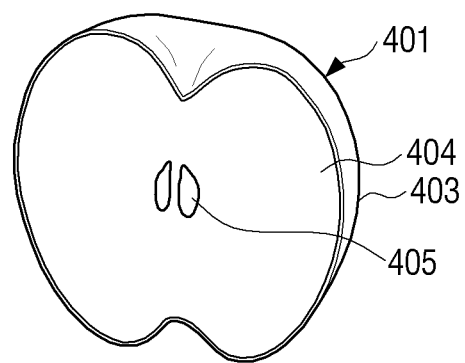
FIG. 13 is a perspective view illustrating a half of an apple printed by the example three-dimensional printing apparatus of FIG. 11.

The above-described three-dimensional printing apparatus 300 may print an object in a three-dimensional shape. For example, when a half of an apple 1 is photographed by the sensing device capable of detecting hardness 10 as illustrated in FIG. 1, and the three-dimensional print data of the half of the apple 1 is formed and sent to the three-dimensional printing apparatus 300, the three-dimensional printing apparatus 300 as illustrated in FIG. 11 may print a half of an apple 401 having a shape corresponding to the half of the apple 1 of FIG. 1. FIG. 13 illustrates an example of the half of the apple 401 printed by the three-dimensional printing apparatus 300 according to an example embodiment of the present disclosure.

Referring to FIG. 13, the half of the apple 401 printed by the three-dimensional printing apparatus 300 according to an example embodiment of the present disclosure includes peel 403, pulp 404, and seeds 405 in the same or similar way as the real apple 1, and the hardness of the peel 403, the pulp 404, and the seeds 405 are different. Also, when the half of the apple 1 is photographed by the sensing device capable of detecting hardness 40 including the camera module 45 as illustrated in FIGS. 4 and 5, the color of the peel 403, the pulp 404, and the seeds 405 of the apple 401 may be printed in the same or similar color as the peel 3, the pulp 4, and the seeds 5 of the real apple 1 (see FIG. 10).

Figure 14:
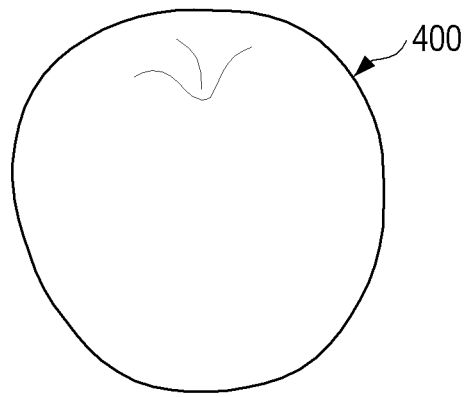
FIG. 14 is a perspective view illustrating an apple printed by the example three-dimensional printing apparatus of FIG. 11.

In the case where terahertz wave sensors or millimeter wave sensors are used as the plurality of sensors of the sensor array and the three-dimensional print data is formed by photographing an uncut apple using the frequency sweep, the three-dimensional printing apparatus 300 according to an example embodiment of the present disclosure can print an apple 400 having the same shape as a real apple as illustrated in FIG. 14. Accordingly, when the apple 400 formed by the three-dimensional printing apparatus 300 according to an example embodiment of the present disclosure as illustrated in FIG. 14 is cut in half, the same structure as that of a real apple having the peel 403, the pulp 404, and the seeds 405 may be confirmed as illustrated in FIG. 13.

By using a sensing device capable of detecting hardness according to an example embodiment of the present disclosure, three-dimensional print data including hardness information or three-dimensional print data including hardness information and color information may be formed.

With a mobile device according to an example embodiment of the present disclosure, three-dimensional print data including hardness information and color information may be formed using a sensing device capable of detecting hardness and a camera module.

Also, with a three-dimensional printing apparatus according to an example embodiment of the present disclosure, an object having hardness and color similar to those of a real object may be printed using the three-dimensional print data formed by a sensing device capable of detecting hardness and a mobile device as described above.

While the various example embodiments of the present disclosure have been described, additional variations and modifications of the embodiments may occur to those skilled in the art once they learn the technical features of the present disclosure. Therefore, it is intended that the appended claims shall be understood to include both the above embodiments and all such variations and modifications that fall within the spirit and scope of the disclosure.

What is claimed is:

1. A sensing device capable of detecting hardness comprising:
   a sensor array comprising a plurality of sensors arranged in a matrix form, wherein each of the plurality of sensors includes a transmitter configured to emit a detection wave and a receiver configured to receive a reflected wave; and a controller configured to obtain image information and hardness information of each portion of an object from reflected waves received by the plurality of sensors, and to form three-dimensional print data by mapping the image information and the hardness information.

2. The sensing device capable of detecting hardness of claim 1, wherein
the plurality of sensors of the sensor array are arranged in a plane.

3. The sensing device capable of detecting hardness of claim 1, wherein
the plurality of sensors of the sensor array are arranged in a hollow cylindrical shape.

4. The sensing device capable of detecting hardness of claim 3, wherein
the sensor array further comprises a plurality of sensors provided to cover one end of the hollow cylindrical shape.

5. The sensing device capable of detecting hardness of claim 1, further comprising:
a plurality of camera modules provided in the sensor array, each camera module comprising a camera,
wherein the controller is configured to obtain color information of each portion of the object from one or more of the plurality of camera modules.

6. The sensing device capable of detecting hardness of claim 1, wherein
the sensor array comprises a plurality of first sensors configured to emit a first detection wave, and a plurality of second sensors configured to emit a second detection wave different from the first detection wave.

7. The sensing device capable of detecting hardness of claim 6, wherein
the first detection wave comprises a terahertz wave, and the second detection wave comprises an ultrasonic wave.

8. The sensing device capable of detecting hardness of claim 5, wherein
the controller is configured to form the three-dimensional print data by mapping the image information, the hardness information, and the color information, and to store the three-dimensional print data.

9. The sensing device capable of detecting hardness of claim 1, wherein
each of the plurality of sensors is configured to emit a detection wave comprising one or more of a terahertz wave, a millimeter wave, and an ultrasonic wave.

10. A mobile device comprising:
a camera module comprising a camera;
a sensor array disposed adjacent to the camera module and comprising a plurality of sensors arranged in a matrix form, wherein each of the plurality of sensors includes a transmitter configured to emit a detection wave and a receiver configured to receive a reflected wave; and
a controller configured to obtain image information and hardness information of each portion of an object from reflected waves received by the plurality of sensors, to obtain color information of each portion of the object from the camera module, and to form three-dimensional print data by mapping the image information, the hardness information, and the color information.

11. The mobile device of claim 10, wherein
the controller is configured to store the three-dimensional print data.

12. The mobile device of claim 10, further comprising:
a cylindrical sensor array detachably connected to the mobile device.

13. The mobile device of claim 12, wherein
the cylindrical sensor array comprises a plurality of camera modules.

14. The mobile device of claim 10, further comprising:
an ultrasonic sensor array unit comprising an ultrasonic sensor detachably connected to the mobile device.

15. A three-dimensional printing apparatus, comprising:
a receiver comprising receiving circuitry configured to receive three-dimensional print data from a sensing device capable of detecting hardness;
a print controller configured to analyze the three-dimensional print data received by the receiver;
a material mixing portion comprising a mixer configured to form a material corresponding to an analysis result of the print controller; and
a print head configured to form a shape corresponding to the received three-dimensional print data using the material supplied from the material mixing portion,
wherein the sensing device capable of detecting hardness comprises,
a sensor array comprising a plurality of sensors arranged in a matrix form; and
a controller configured to obtain image information and hardness information of each portion of an object from reflected waves received by the plurality of sensors, and to form three-dimensional print data by mapping image information and hardness information.

16. The three-dimensional printing apparatus of claim 15, wherein
the material mixing portion comprises,
a material selecting portion comprising at least one material container configured to supply a material having hardness corresponding to the analysis result of the print controller;
a color selecting portion comprising at least one color pigment container configured to supply a pigment having a color corresponding to the analysis result of the print controller; and
a mixing portion comprising a mixer configured to form a material having color and hardness corresponding to the analysis result of the print controller by mixing the material supplied from the material selecting portion and the pigment supplied from the color selecting portion.

17. The three-dimensional printing apparatus of claim 16, wherein
the material selecting portion includes a plurality of material cartridges accommodating materials having different hardness.

18. The three-dimensional printing apparatus of claim 16, wherein
the color selecting portion includes a plurality of pigment cartridges accommodating pigments having different colors.

19. The three-dimensional printing apparatus of claim 15, wherein
the receiver is configured to receive the three-dimensional print data from a cloud or a Web hard disk.

20. The three-dimensional printing apparatus of claim 15, wherein the sensing device capable of detecting hardness is provided in a mobile device having a camera module comprising a camera, and wherein the receiver receives the three-dimensional print data from the mobile device.

* * * * *